United States Patent [19]

Kumar et al.

[11] Patent Number: 5,200,510
[45] Date of Patent: Apr. 6, 1993

[54] METHOD FOR PURIFYING FACTOR VIII:C, VON WILLEBRAND FACTOR AND COMPLEXES THEREOF

[75] Inventors: Anur A. Kumar; Frederick S. Hagen; Andrzej Z. Sledziewski, all of Seattle, Wash.

[73] Assignee: ZymoGenetics, Inc., Seattle, Wash.

[21] Appl. No.: 162,877

[22] Filed: Mar. 2, 1988

Related U.S. Application Data

[63] Continuation-in-part of Ser. No. 62,896, Jun. 16, 1987, abandoned.

[51] Int. Cl.$^5$ ............................ C07K 3/18; C07K 3/20
[52] U.S. Cl. ...................................... 530/383; 530/413
[58] Field of Search ................................. 530/413, 383

[56] References Cited

U.S. PATENT DOCUMENTS

Re. 32,011 10/1985 Zimmerman et al. .............. 424/101

OTHER PUBLICATIONS

Honda et al. 1986, J. Biol. Chem. 261(27):12579-12585.
Wicki et al. 1985, Eur. J. Biochem. 153:1-11.
Wilchek et al. 1984, Methods in Enzymology, 104:3-55.
Cuatrecasas et al 1971, Ann. Rev. Biochem. 40:259-278.

*Primary Examiner*—Robert A. Wax
*Assistant Examiner*—Keith C. Furman
*Attorney, Agent, or Firm*—Seed and Berry

[57] ABSTRACT

Methods for purifying factor VIII:C, von Willebrand factor (vWF) or complexes thereof from heterogeneous biological fluids are disclosed. The methods utilize a binding peptide, specific to either factor VIII:C or vWF, bound to an insoluble matrix. Peptides suitable for use within the methods are also disclosed.

21 Claims, 2 Drawing Sheets

METHOD FOR PURIFYING FACTOR VIII:C, VON WILLEBRAND FACTOR AND COMPLEXES THEREOF

CROSS-REFERENCE TO RELATED APPLICATION

This application is a continuation-in-part of U.S. patent application Ser. No. 062,896, filed Jun. 16, 1987, which application is now abandoned.

TECHNICAL FIELD

The present invention is directed toward methods for purifying proteins in general, and more specifically, to methods for purifying factor VIII:C, von Willebrand factor and complexes thereof from heterogeneous biological fluids.

BACKGROUND ART

Factor VIII:C procoagulant protein (also known as "Antihemophilic Factor") is a participant in the intrinsic pathway of blood coagulation, acting as a cofactor in the activation of factor X. Factor VIII:C procoagulant protein (factor VIII:C) circulates at low concentration (about 200 ng/ml) in the plasma as a non-covalently linked complex with von Willebrand factor (vWF).

Several hereditary disorders are associated with these two proteins. In individuals with the hereditary X chromosome-linked bleeding disorder, hemophilia A (also known as "classic hemophilia"), factor VIII:C activity is absent. Hemophilia A is the most common hereditary disorder of coagulation, affecting about six men in every 100,000 (Bloom, Nature 303:474-475, 1983). Von Willebrand's disease is a hereditary bleeding disorder which results in extended bleeding time due to reduced levels of active vWF. This disorder affects about one person in every 100,000 (L. Harke, Hemostatis Manual, 2d ed., F. A. Davis Co., Philadelphia, Pa., 1974). Currently, individuals affected by these two bleeding disorders are treated with concentrates rich in factor VIII:C and vWF. These protein concentrates, prepared from the pooled blood of a large number of donors, are expensive to produce and, though enriched for the specific factors required, still contain less than 1% factor VIII:C and are contaminated with other proteins. In addition, there is a risk of viral contamination (e.g., hepatitis viruses and HIV-I) in the concentrates due to the use of pooled human plasma as the source of these coagulation factors and many hemophiliacs receiving the concentrates have been infected.

Purification of factor VIII:C has been complicated by its low abundance in plasma, extreme lability, and association with von Willebrand factor. Although expression of cloned factor VIII:C in recombinant cells has been achieved (Wood et al., Nature 312:330-337, 1984; Toole et al., Nature 312:342-347, 1984; Truett et al., DNA 4:333-349, 1985), the recombinant proteins have not been extensively purified or characterized.

A number of purification methods for factor VIII:C have been attempted, although they are characterized by somewhat limited efficiency. For instance, Farrugia et al. (Thromb. Haemost. 51:338-342, 1984) described a factor VIII:C purification method which involved precipitation of factor VIII:C from plasma or cryoprecipitate with hydrophilic polymers, while Wagner et al. (Thromb. Diath. Haemorrh. 11:64, 1964) described the purification of factor VIII:C from plasma or cryoprecipitate using precipitation with lecithins. In addition, Madaras et al. (Haemost. 7:321-331, 1978) have described the purification of factor VIII:C from plasma or cryoprecipitate using chromatography on ion-exchange columns and gel filtration followed by heparin-sepharose affinity chromatography. Knutson and Fass (Blood 59:615-624, 1982) described a multistep process for the purification of porcine factor VIII:C. In general, these methods produce factor VIII:C in low yields and, in many cases, as a complex with vWF.

The preparation of highly purified bovine factor VIII:C derived from bovine plasma has been described by Vehar and Davie (Biochemistry 19:401-410, 1980) using gel filtration and chromatography on a factor X-sepharose column as the final step of the purification procedure. Tuddenham et al. (J. Lab. Clin. Med. 93:40-53, 1979) have described a method for purifying factor VIII:C using immunoaffinity chromatography. This method utilizes polyclonal antisera directed against vWF to adsorb the factor VIII:C-vWF complex from plasma. Purified factor VIII:C is eluted from the column using a calcium ion gradient. Austen (British J. Haemat. 43:669, 1979) described a method for separating factor VIII:C from contaminating plasma proteins using aminohexyl sepharose chromatography. These methods do not, however, result in a concentrated product.

Zimmerman and Fulcher (U.S. Pat. No. 4,361,509; 1982) have disclosed a method for preparing a concentrated high-purity factor VIII:C using a two-column method. The first column, consisting of monoclonal antibodies directed against vWF bound to agarose beads, served to purify factor VIII:C from the starting material. The second column, used for concentration of the purified factor VIII:C, consisted of aminohexyl-substituted agarose.

The major disadvantages posed by the use of immunoaffinity chromatography, as described by Tuddenham et al. (ibid.) and Zimmerman and Fulcher (ibid.), are in the regeneration and reusability of the affinity matrix and the contamination of the product with non-human antibodies. Immunoaffinity columns, as described above, bind the vWF portion of the factor VIII:C-vWF complex. Calcium ion treatment of the immunoaffinity column releases free factor VIII:C, but the vWF remains tightly bound to the column. However, the factor VIII:C purified by this method is often contaminated with nonhuman antibodies that have been leached from the column. Further, the tight bond between antibody and vWF necessitates the use of powerful desorption agents to achieve elution of the bound vWF as a prelude to reuse of the column. These procedures can lead to loss of the biological activity of the vWF and/or loss of the immunological properties of the antibody, resulting in a short-lived column. Use of such columns for the commercial preparation of factor VIII:C is therefore expensive, while their use for the isolation of biologically active vWF is difficult at best. Additionally, the use of strong desorption agents, some of which are toxic to human systems, requires their removal from the product before use.

In view of the disadvantages of current methods employed for purifying factor VIII:C and vWF, there is a need in the art for an alternative purification method which provides a high yield of pure factor VIII:C, vWf and/or the factor VIII:C-vWF complex. The present invention fulfills this need, and further provides other related advantages.

DISCLOSURE OF THE INVENTION

Briefly stated, the present invention discloses method for purifying factor VIII:C (FVIII:C), von Willebrand factor (vWF) or complexes thereof from heterogeneous biological fluids. The methods utilize a binding peptide, specific to either factor VIII:C or vWF, bound to an insoluble matrix.

In one aspect of the present invention directed toward purifying vWF, the method generally comprises (a) exposing the biological fluid to a peptide that specifically binds to vWF comprising at least a portion of the amino terminal 340 amino acids of glycoprotein Ib, the peptide being bound to an insoluble matrix, such that the vWF specifically binds to the peptide; (b) eluting the bound vWF from the peptidel and (c) collecting the vWF-containing eluate. The method may also include washing nonspecifically bound elements from the matrix, as well as concentrating the vWF subsequent to the step of collecting. Within a preferred embodiment, the step of eluting comprises exposing the bound vWF to a pH gradient or a high salt buffer. Within certain embodiments, the peptide consists of between approximately four and forty amino acids and comprises a sequence corresponding to a portion of amino acids 165-260 of glycoprotein Ib. The peptide may also be a peptide such as PEP-12, PEP-13, PEP-14, PEP-15, PEP-16 or PEP-17.

Within another aspect of the present invention, directed toward purifying factor VIII:C-vWF complexes, the method generally comprises (a) exposing the biological fluid to a peptide that specifically binds to von Willebrand factor, the peptide being bound to an insoluble matrix such that the factor VIII:C-vWF complex specifically binds to the peptide; (b) eluting the bound factor VIII:C-vWF complex from the peptide; and (c) collecting the factor VIII:C-vWF complex-containing eluate. The method may also include washing nonspecifically bound elements from the matrix as well as concentrating the collected complex.

Within a third aspect of the present invention, directed toward purifying factor VIII:C from a heterogeneous biological fluid, the method generally comprises (a) exposing the biological fluid to a peptide that specifically binds to von Willebrand factor (vWF), the vWF being complexed with factor VIII:C, the peptide being bound to an insoluble matrix, such that the factor VIII:C-vWF complex specifically binds to the peptide; (b) eluting the factor VIII:C from the complex; and (c) collecting the factor VIII:C-containing eluate. Within preferred embodiments, the peptide comprises at least a portion of factor X or factor IX. Within a particularly preferred embodiment, the peptide comprises all or a portion of glycoprotein Ib. The method may also include washing nonspecifically bound elements from the matrix, as well as concentrating the factor VIII:C subsequent to the step of collecting.

Another aspect of the present invention, directed toward purifying factor VIII:C, discloses a method generally comprising (a) dissociating the factor VIII:C-vWF complex within a heterogeneous biological fluid; (b) exposing the dissociated complex to a peptide that specifically binds to factor VIII:C, the peptide being bound to an insoluble matrix, such that the factor VIII:C specifically binds to the peptide; (c) eluting the bound factor VIII:C from the peptide; and (d) collecting the factor VIII:C-containing eluate. The method may also include a washing step and/or concentrating step as described above.

Within yet another aspect of the present invention, directed toward purifying factor VIII:C from a heterogeneous biological fluid containing FVIII:C-vWF complexes, the method generally comprises: (a) exposing the biological fluid to a peptide that specifically binds to either FVIII:C or vWF, the peptide being bound to an insoluble matrix, such that the FVIII:C-vWF complex specifically binds to the peptide; (b) eluting the bound complex from the peptide; (c) dissociating the FVIII:C-vWF complex; and isolating the FVIII:C.

The present invention also discloses peptides suitable for use within the methods described above. These and other aspects of the present invention will become evident upon reference to the following detailed description and attached drawing.

BRIEF DESCRIPTION OF THE DRAWING

Figure 1A:
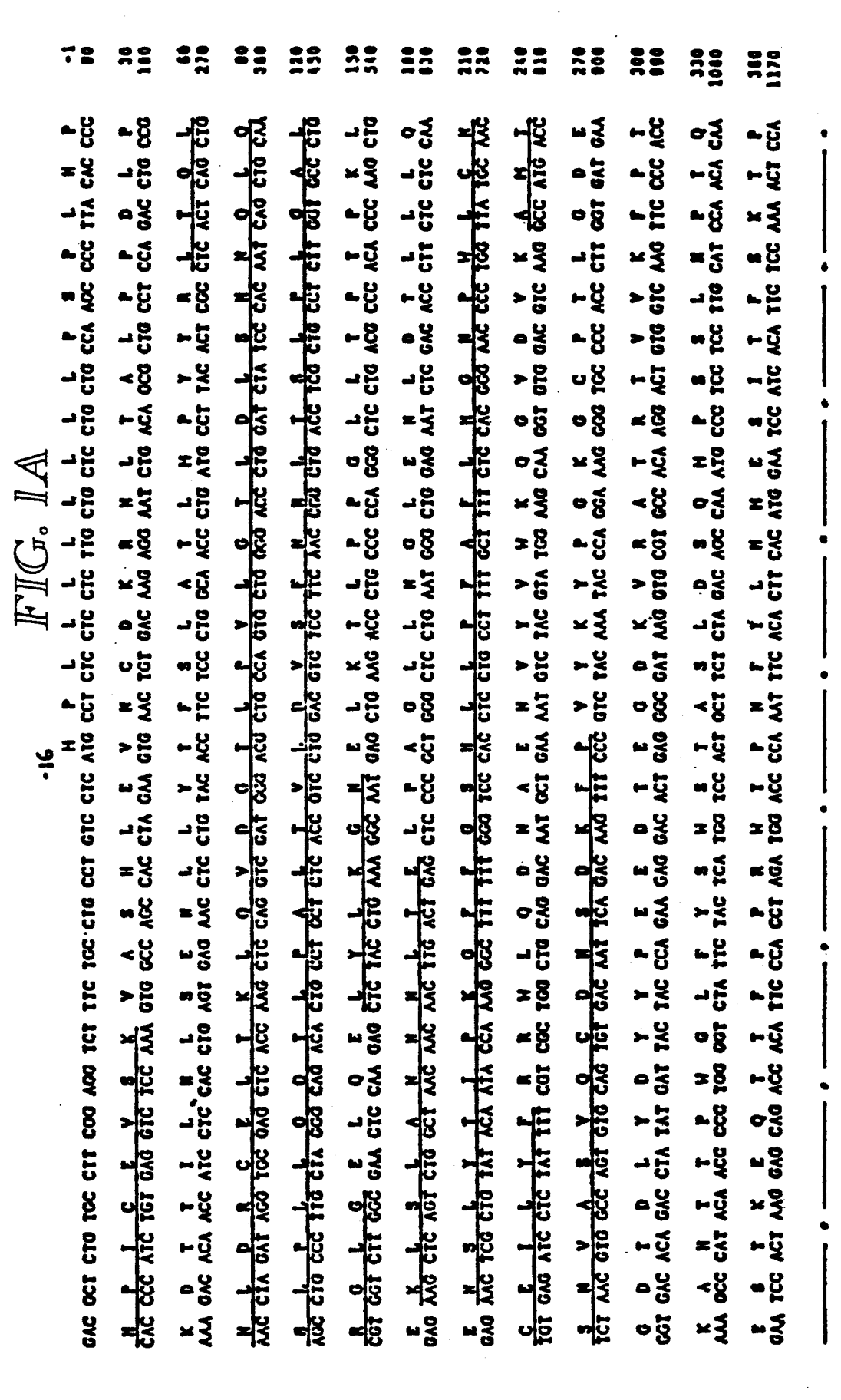
Figure 1B:
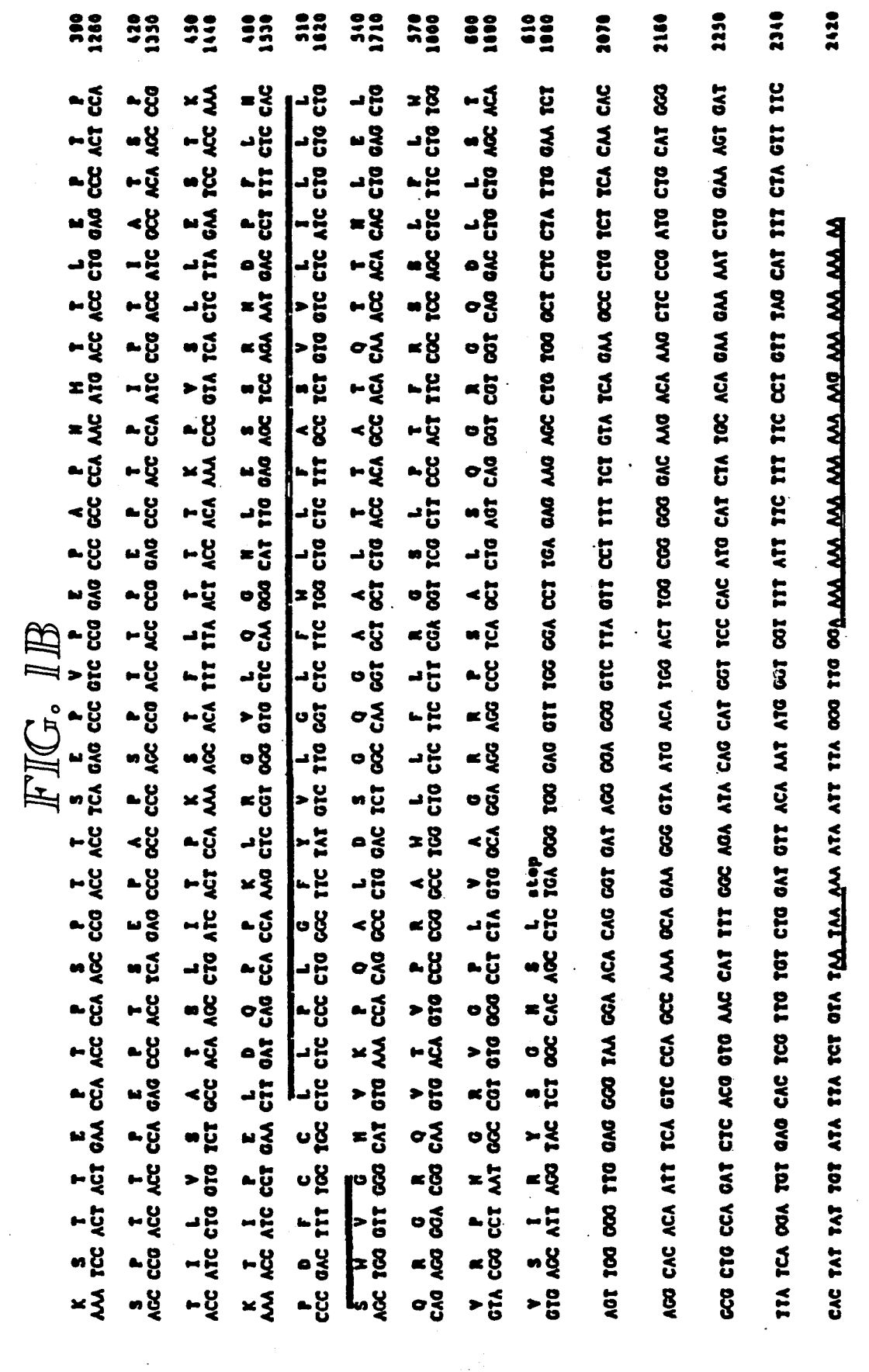

FIGS. 1A and 1B depict the nucleotide sequence and predicted amino acid sequence for a cDNA encoding the α chain of human glycoprotein Ib (GPIb). The amino terminus of the mature protein starts with +1, whereas the negative numbers (−16 through −1) represent the signal peptide.

BEST MODE FOR CARRYING OUT THE INVENTION

Prior to setting forth the invention, it may be helpful to an understanding thereof to define certain terms to be used hereinafter.

Heterogeneous Biological Fluid: Any fluid containing cells, portions of cells, or cell products and including one or more proteins. Heterogeneous biological fluids include, but are not limited to, blood, plasma, serum, cell lysates, cell-conditioned media and fractions thereof.

As noted above, the present invention provides a method for purifying factor VIII:C and/or vWF utilizing a binding peptide specific to either factor VIII:C or vWF, bound to an insoluble matrix. The use of binding peptides to purify factor VIII:C, vWF and complexes thereof has major advantages over current purification methods. A binding peptide, as described above, preferably of 40 amino acids or less, may be commercially synthesized at a fraction of the cost of producing antibodies specific to vWF or factor VIII:C. Further, the binding peptides described herein bind vWF or factor VIII:C in a non-covalent manner such that the product may be eluted as a complex (vWF-factor VIII:C) or as a pure product (factor VIII:C or vWF alone). Elution of the products using high ionic strength buffers will not damage the binding peptide and will result in a column that is ready for reuse with a minimum of pretreatment. Another major advantage of the invention is that the binding peptide is of human origin. In the event that some of the binding peptide becomes uncoupled from the matrix and contaminates the product, it will be less immunogenic compared to heterologous antibodies, and the small size of the peptide will result in its rapid clearance from the plasma. As a result, any peptide contaminants present in the final preparation should not interfere with the normal function of the product.

Binding peptides suitable for use in purifying factor VIII:C and/or von Willebrand factor may be derived from glycoprotein Ib, factor IX, factor X, von Willebrand factor and factor VIII. These proteins interact with factor VIII:C or vWF in a specific manner.

In plasma, vWF and factor VIII:C exist as a noncovalently bound complex (for review, see L. W. Hoyer, *Blood* 58:1-13, 1981). The two proteins may be separated by treatment with a high ionic strength buffer, such as 0.25M-0.5M $CaCl_2$ or 1M NaCl.

Glycoprotein Ib (GPIb) is a platelet receptor which interacts with vWF to facilitate the adhesion of platelets to exposed subendothelial collagen. GPIb is a heterodimer composed of disulfide-linked α- and β-chains, the α-chain being the chain which contains the vWF binding domain (Okumura et al., *J. Biol. Chem.* 253:3435-3443, 1978).

Binding peptides for use in carrying out the present invention may be isolated by one of three general methods. The first method involves the synthesis of overlapping peptides of about 10 to 40 amino acids, preferably about 20 amino acids, in length. Such peptides may be synthesized according to procedures which are well known in the art (Merrifield, *J. Am. Chem. Soc.* 85:2149-2154, 1963; Houghten, *Proc. Natl. Acad. Sci. USA* 82:5131-5135, 1985) or the peptides may be manufactured upon request through such commercial suppliers as Applied Biosystems (Foster City, Calif.), or Biosearch (San Rafael, Calif.). The peptides correspond to the amino acid sequence of one of the binding proteins (glycoprotein Ib, factor IX, factor X or vWF) or a suitable portion of the binding protein. The peptides are then bound to an insoluble matrix or support, such as a microtiter plate, and a solution containing factor VIII:C, von Willebrand factor, or factor VIII:C-vWF complex is added. After an incubation period, unbound protein is removed and labeled antibodies directed against factor VIII:C or vWF are added. After incubation, excess antibodies are removed and the amount of bound antibody is measured. The amount of antibody bound is proportional to the ability of the peptide to bind the protein of interest. Alternatively, binding may be measured directly using labeled factor VIII:C or vWF.

A second method of identifying binding peptides relies on genetic engineering techniques to determine a suitable binding region of the binding protein involved in the specific interaction. A cDNA sequence encoding the binding protein is cloned into a plasmid vector such that expression of the cDNA is under the control of a phage T7 promoter. The plasmid is isolated and transcribed in vitro essentially as described by Melton et al. (*Nuc. Acids Res.* 12:7035-7056, 1984), using T7 polymerase. The resultant RNA is used as a template for cDNA cloning by the random priming method (Maniatis et al., eds., *Molecular Cloning: A Laboratory Manual,* Cold Spring Harbor Laboratory, 1982), and the cDNA thus produced is used to prepare a λgt11 expression library (Young and Davis, *Proc. Natl. Acad. Sci. USA* 80:1194, 1983). The library is screened by the ligand blotting technique (Sikela and Hahn, *Proc. Natl. Acad. Sci. USA* 84:3038-3042, 1987) using the labeled protein of interest as a probe. Clones which express binding peptides are mapped to determine the precise location and sequence of a suitable binding peptide.

A third method of isolating suitable peptides relies on digestion of purified binding proteins by limited proteolytic and chemical cleavage. Suitable digestion methods include CNBr cleavage and cleavage with proteolytic enzymes, such as trypsin, chymotrypsin, lysine endopeptidase or *S. aureus* V-8 protease. The proteins are isolated from plasma sources (for example, as described by Chopek et al., *Biochemistry* 25:3146-3155, 1986 or Osterud and Rapaport, *Proc. Natl. Acad. Sci. USA* 74:5260-5264, 1977) or are produced in recombinant cells (e.g., Hagen et al., EP 200,421). DNA sequences encoding factor IX (Kurachi and Davie, *Proc. Natl. Acad. Sci. USA* 79:6461-6464, 1982; Anson et al., *Nature* 315:683-685, 1985), factor X (Leytus et al., *Proc. Natl. Acad. Sci. USA* 81:3699-3702, 1984; Leytus et al., *Biochemistry* 25:5098-5102, 1986), von Willebrand factor (Sadler et al., *Proc. Natl. Acad.* Sci. USA 82:6394-6398, 1985; Ginsberg et al., *Science* 228:1401-1406, 1985) and factor VIII (Toole et al., *Nature* 312:342-347, 1984) have been described.

Binding peptides specific to either vWF or factor VIII:C are identified and synthesized as described above and are subsequently coupled to one of a variety of commercially available insoluble matrices. Exemplary matrices include CNBr-activated sepharose 4B (Pharmacia, Sweden), AH-sepharose 4B (Pharmacia), CH-sepharose 4B (Pharmacia), activated CH-sepharose 4B (Pharmacia), Affi-Gel (Bio-Rad, Richmond, Calif.) and Reacti-Gel (GF-2000) (Pierce Chemical Company, Rockford, Ill.). The coupling reaction used to bind the peptide to the matrix is one of a variety of procedures known in the literature. Coupling reactions may use any of the following peptide functions: the amino function of the peptide or ligand (Axen et al., *Nature* 214:302, 1967; Bethell et al., *J. Biol. Chem.* 254:2572-2574, 1979; B. S. Coller, *Blood* 55:169, 1980); the carboxy function of the peptide or ligand (B. T. Kaufman and J. V. Pierce, *Biochem. Biophys. Res. Commun.* 44:608-613, 1971); or thiol groups (L. Ruden and H. F. Deutsch, *J. Biol. Chem.* 253:519-524, 1978). Spacers between the column matrix and the binding peptide may also be used to enhance the efficiency of purification (Pantoliano et al., *Biochem.* 23:1037-1042, 1984). It may be desirable to add a lysine or cysteine residue to the end of the peptide to facilitate coupling to the matrix. As noted above, the affinity purification system described herein may be used to purify factor VIII:C or von Willebrand factor or complexes thereof from a variety of heterogeneous biological fluids. These include plasma, plasma-derived concentrates and cell lysates and media from recombinant cells. Methods for producing factor VIII:C in recombinant cells are described by Wood et al. (ibid), Toole et al. (ibid) and Truett et al. (ibid). Kaufman and Adamson (WO 87/04187) disclose methods of producing factor VIII:C-type proteins using recombinant cells which are cultured in the presence of vWF.

For purification of factor VIII:C, vWF or factor VIII:C-vWF complex, the biological fluid is exposed to the matrix-bound peptide under conditions such that vWF or factor VIII:C-vWF complex binds to the peptide. Subsequent to the step of exposing, it is preferred that nonspecifically bound elements be washed from the column. The column may be washed with a low ionic strength buffer of approximately neutral pH, preferably the same buffer used in loading the column. a particularly preferred buffer is 20 mM imidazole, pH 6.8 containing 150 mM NaCl. The bound complex or the protein of interest is then eluted from the column and collected. For purification of factor VIII:C or vWF, elution may be achieved through the use of a pH gradient or a high ionic strength buffer. Factor VIII:C-vWF complex is preferably eluted through the use of a pH gradient. To purify factor VIII:C from factor VIII:C-vWF complex, the factor VIII:C is either eluted from the column using a high ionic strength buffer or the complex is eluted and subsequently dissociated in a high ionic strength buffer. In a preferred embodiment, the collected protein is concentrated. Preferred methods of concentrating include lyophilization and the use of commercially available (e.g., Amicon) concentration units.

The following examples are offered by way of illustration, and not by way of limitation.

EXAMPLES

Example 1

Binding assay for detection and characterization of factor VIII:C binding peptides Factor VIII:C binding is directly assayed using a factor VIII:C-enriched protein concentrate and radiolabeled monoclonal antibodies directed against factor VIII:C. A 96-well break-apart microtiter plate (Dynatech, Alexandria, Va.) is coated with native protein or peptide. A factor VIII:C-enriched protein concentrate is added to the plate and incubated for one hour. Excess factor VIII:C is removed from the plates after incubation. Radiolabeled monoclonal antibodies, specifically directed against factor VIII:C, are added to the plate and allowed to incubate for one hour. After incubation, excess label is removed and bound antibody is measured.

Alternatively, direct binding may be assayed using the binding peptide-coated plates. Radiolabeled factor VIII:C may be used as a direct measure of factor VIII:C binding to the binding peptide. Radiolabeled vWF may be readily substituted in this assay to identify binding peptides specific for vWF.

Example 2

Identification of the GPIb binding domain for vWF

As noted above, the binding domain for vWF resides in the α-chain of GPIb. The cDNA encoding the α-chain of GPIb has been cloned and sequenced and is shown in the Figure. The binding region is determined by synthesis of 20-amino-acid-long, overlapping peptides covering the first 340 amino acids of the mature α chain of GPIb.

The vWF-factor VIII binding region of GPIb was identified by screening 22 synthetic peptides derived from the amino-terminal half of the GPIb molecule for the ability to bind to the vWF-factor VIII complex. The synthetic peptides (obtained from Biosearch, Inc., San Rafael, Calif.) were designed as 20-residue fragments with a 5-residue overlap between pairs. Affinity gels, prepared by linking the amino groups of the synthetic peptides to amino hexanoic acid activated Sepharose-4B (CH-activated-Sepharose 4B, obtained from Sigma Chemical Co., St Louis, Mo.) were used to screen the peptides for binding. Briefly, the experimental procedure included mixing reconstituted factor VIII concentrate (Alpha Therapeutic Corporation, Los Angeles, Calif.) with the gel bound peptides, washing the resulting complex and eluting the factor VIII activity. The ability of the immobilized GPIb-derived peptides to bind to factor VIII was evaluated by determining the factor VIII activity in the starting material, column wash, and the column elute.

The peptides (5–10 mg) were dissolved in DMSO (2–3 mls), mixed with an equal volume of coupling buffer (0.1M NaHCO$_3$, pH 8.0) and then added to 3–5 mls of swollen, prewashed CH-activated-Sepharose 4B (the gel was processed as suggested by the manufacturer). The mixture was incubated on a rocker at 4° C. for 20 hours. The coupling reaction was continued for one hour at 22° C. the gels were then poured into columns and washed with coupling buffer followed by DMSO. The initial wash (coupling supernate) was saved for analysis. The gels were blocked with 0.2M glycine, pH 8.5 and presaturated with 1% BSA in 20 mM imidazole buffer, pH 6.8, containing 150 mM NaCl (IBS) for 1 hour at 22° C. The peptide-coupled, glycine-blocked, BSA-treated columns were washed extensively with IBS and used in binding experiments as described below. Control columns were prepared by using the same procedure except that the peptide was omitted from the protocol. The extent of coupling was calculated after estimating the amount of peptide in the starting material, coupling supernate and initial washes using the ninhydrin reagent. Using this procedure, 40% to 60% of each peptide was found to be coupled to the affinity chromatography gel.

Factor VIII concentrate, reconstituted in IBS, was mixed with GPIb-peptide-Sepharose and incubated at 22° C. for 2 hours on a rocker. At the end of the incubation period the gel suspension was poured into a column, allowed to settle, and washed with IBS until the absorbance of the effluent as monitored at 280 nm reached the baseline. Factor VIII bound to the column was eluted with IBS containing 0.5M NaCl and 0.2% Tween-80. The flow rate of the solvents during wash and elution was maintained at 0.7 ml per minute.

The factor VIII activity in the starting material, column effluent and eluate was quantitated by the one-stage clotting assay in order to evaluate the performance of the column. Pooled normal human plasma was used as the standard in the clotting assays. Mega-1 factor VIII standard (obtained from Alpha Therapeutic Corporation, Los Angeles, Calif.) was used to calibrate the pooled normal plasma. Factor VIII deficient plasma and pooled normal plasma were obtained from George King Biomedical, Inc., Overland Park, Kans. Clotting assays were done using an MLA-Electra-800 automatic coagulation timer (Medical Laboratory Automation, Inc., New York).

Data from the binding experiments identified four peptides which were capable of binding to the factor VIII in the reconstituted concentrate. These peptides correspond to amino acid segments 165–184, 180–199, 195–214 and 240–259 of GPIb. Primary sequences of these four peptides are shown in Table 1.

TABLE 1

| Amino Acid Sequences of Factor VIII Binding Peptides of GPIb | | |
|---|---|---|
| Region | Sequence | Designation |
| 165–184 | A G L L N G L E N L D T L L L Q E N S L | Pep-12 |
| 180–199 | Q E N S L Y T I P K G F F G S H L L P F | Pep-13 |
| 195–214 | H L L P F A F L H G N P W L C N C E I L | Pep-14 |
| 240–259 | T S N V A S V Q C D N S D K F P V Y K Y | Pep-17 |

Data from the binding experiments are presented in Table 2.

TABLE 2

| | Factor VIII (units) | | | | |
|---|---|---|---|---|---|
| Sample | Pep-12 | Pep-13 | Pep-14 | Pep-17 | CH-Sep |
| Set A Starting Material | 62 | 62 | 62 | 62 | 62 |

TABLE 2-continued

| Sample | Factor VIII (units) | | | | |
|---|---|---|---|---|---|
| | Pep-12 | Pep-13 | Pep-14 | Pep-17 | CH-Sep |
| Effluent | 42.4 | 11.6 | 22 | 20.2 | 60.8 |
| | (69) | (19) | (36) | (33) | (98) |
| Eluate | 7.8 | 14 | 16.8 | 21.6 | 1.6 |
| | (13) | (23) | (27) | (35) | (2.6) |
| Set B Starting Material | 27.4 | 27.4 | 27.4 | 27.4 | 27.4 |
| Effluent | 24 | 6.2 | 12.2 | 8.0 | 28 |
| | (88) | (22.6) | (44.5) | (29.2) | (102) |
| Eluate | 3.2 | 5.0 | 11.2 | 7.4 | NA |
| | (11.7) | (18.3) | (40.9) | (27) | |

In set B the gels were precleaned with water and 50% $CH_3CN$ followed by IBS pH 6.8 prior to the experiment. NA: Elution of factor VIII was not attempted.

The numbers in parentheses represent percent factor VIII in those fractions.

The data presented in Table 2 indicate that the vWF-factor VIII binding region of GPIb is situated between amino acid residues 165 and 260 of the protein. The data also support the concepts that the binding site is made up of amino acids from a linear stretch of residues in the GPIb molecule and peptides derived from this region can be used for affinity purification of factor VIII or vWF-factor VIII complexes. Based on these results, it is predicted that peptides derived from amino acid residues 215 to 239 of GPIb are involved in the binding of the vWF-factor VIII complex. The sequences of two overlapping peptides representing this region (designated Pep-15 and Pep-16) are shown in Table 3.

TABLE 3

| Region | Sequence | Designation |
|---|---|---|
| 210–229 | N C E I L Y F R R W L Q D N A E N V Y V | Pep-15 |
| 225–244 | E N V Y V W K Q G V D V K A M T S N V A | Pep-16 |

Example 3

Identification of the binding domain for factor VIII:C on vWF

The binding domain for factor VIII:C on vWF is determined using limited proteolytic and chemical cleavage of vWF. vWF is purified by the method described by Chopek et al. (Biochem. 25:3146–3155, 1986). The purified vWF is subjected to degradation using CNBr cleavage (E. Gross and B. Witkop, J. Biol. Chem. 237:1856–1860, 1962) to generate vWF peptides. Alternatively, peptides are generated by using, for example, trypsin, chymotrypsin, lysine endopeptidase, or Staphylococcus aureus V-8 protease (Chopek et al., ibid.).

The peptide mixture from the chemical or enzymatic digestion of vWF is subjected to chromatography on an HPLC/gel-permeation column (GF-250, Dupont). Following this initial purification, the individual peaks from the gel-permeation column are subjected to further purification on HPLC columns using water-acetonitrite or water-n-propanol gradients containing 0.1% trifluoroacetic acid.

Alternatively, overlapping peptides may be synthesized on the basis of the amino acid sequence for von Willebrand factor (Titani et al., Biochemistry 25:3171–3184, 1986).

The purified peptides are used in binding assays as described in Example 1 and Example 2.

Example 4

Identification of binding domains for factor VIII:C on factor X and IX

Factors X and IXa are purified by the method described by Modi et al. (Thromb. Res. 36:537–547, 1984). Purified peptides derived from these purified factors, native as well as reduced alkylated forms, are generated using the chemical and enzymatic procedures described in Examples 2 and 3.

The peptides are screened using binding assays as described in Example 1 and Example 2.

Example 5

Affinity purification using a binding peptide specific for vWF

An affinity matrix (e.g., prepared as described in Example 2) is incubated with a sample containing factor VIII:C. This mixture is incubated overnight at 4° C. The affinity matrix with bound factor VIII:C or vWF-factor VIII:C complex is then packed into a column and washed with appropriate buffers (i.e., 20 mM imidazole-HCl, pH 6.8, 10 mM $CaCl_2$ or 10% glycerol). Elution of specifically bound factor VIII:C is accomplished by washing this column with a calcium or sodium ion gradient. The bound factor VIII:C elutes at approximately 0.3M $CaCl_2$. Bound factor VIII:C-vWF complex is eluted from the column with a pH gradient. If desired, the eluted complex may be dissociated by $CaCl_2$ treatment and the factor VIII:C and/or vWF recovered by size fractionation (e.g., gel filtration).

Example 6

Affinity purification using a vWF-derived peptide

A factor VIII:C-binding peptide is derived from von Willebrand factor as described in Example 3. The peptide, preferably containing a terminal lysine or cysteine residue, is coupled to a solid matrix as described in Example 2.

A sample of factor VIII:C-vWF complex is adjusted to 0.3M to 0.5M $CaCl_2$. The sample is then mixed with the prepared affinity matrix and the $CaCl_2$ concentration of the mixture is reduced to permit binding of the factor VIII:C to the matrix. The mixture is then packed into a column and washed with a suitable buffer. The bound factor VIII:C is eluted from the washed column with 0.3M to 0.5M $CaCl_2$.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for purifying von Willebrand factor from a heterogeneous biological fluid, comprising:
   exposing the biological fluid to a peptide that specifically binds to von Willebrand factor, said peptide consisting essentially of between four and ninety-six amino acids and containing a sequence of at least four consecutive amino acids corresponding to amino acids 165–260 of glycoprotein Ib, said peptide bound to an insoluble matrix such that the von Willebrand factor specifically binds to said peptide;

eluting the bound von Willebrand factor from the peptide; and collecting the von Willebrand factor-containing eluate.

2. The method of claim 1 including, subsequent to the step of exposing, washing non-specifically bound elements from the matrix.

3. The method of claim 1 including, subsequent to the step of collecting, concentrating the von Willebrand factor.

4. The method of claim 1 wherein the step of eluting comprises exposing the bound von Willebrand factor to a pH gradient or a buffer having a salt concentration sufficient to elute said bound von Willebrand factor.

5. The method of claim 1 wherein said peptide consists of between approximately four and forty amino acids and comprises a sequence of at least four consecutive amino acids corresponding to amino acids 165–260 of glycoprotein Ib.

6. The method of claim 1 wherein said peptide is selected from the group consisting of PEP-12, PEP-13, PEP-14, PEP-15, PEP-16 and PEP-17.

7. A method for purifying a factor VIII:C-von Willebrand factor complex from a heterogeneous biological fluid, comprising:

exposing the biological fluid to a peptide that specifically binds to von Willebrand factor, said peptide consisting essentially of between four and ninety-six amino acids and containing a sequence of at least four consecutive amino acids corresponding to amino acids 165–260 of glycoprotein Ib, said peptide bound to an insoluble matrix such that the factor VIII:C-von Willebrand factor complex specifically binds to said peptide;

eluting the bound factor VIII:C-von Willebrand factor complex from the peptide; and collecting the factor VIII:C-von Willebrand factor complex-containing eluate.

8. The method of claim 7 including, subsequent to the step of exposing, washing non-specifically bound elements from the matrix.

9. The method of claim 7 including, subsequent to the step of collecting, concentrating the factor VIII:C-von Willebrand factor complex.

10. The method of claim 7 wherein the step of eluting comprises exposing the bound von Willebrand factor to a pH gradient.

11. The method of claim 7 wherein said peptide consists of between approximately four and forty amino acids and comprises a sequence of at least four consecutive amino acids corresponding to amino acids 165–260 of glycoprotein Ib.

12. The method of claim 7 wherein said peptide is selected from the group consisting of PEP-12, PEP-13, PEP-14, PEP-15, PEP-16 and PEP-17.

13. A method for purifying factor VIII:C from a heterogeneous biological fluid containing factor VIII:C-von Willebrand factor complexes, comprising:

exposing the biological fluid to a peptide that specifically binds to von Willebrand factor said peptide consisting essentially of between four and ninety-six amino acids and containing a sequence of at least four consecutive amino acids corresponding to amino acids 165–260 of glycoprotein Ib, said peptide bound to an insoluble matrix, such that the factor VIII:C-von Willebrand factor complex specifically binds to said peptide;

eluting the factor VIII:C from the complex; and collecting the factor VIII:C-containing eluate.

14. The method of claim 13 wherein said peptide consists of between approximately four amino acids and forty amino acids.

15. The method of claim 13 wherein said peptide includes a terminal lysine or cysteine residue.

16. The method of claim 13 including, subsequent to the step of exposing, washing non-specifically bound elements from the matrix.

17. The method of claim 13 including, subsequent to the step of collecting, concentrating the factor VIII:C.

18. The method of claim 13 wherein the step of eluting comprises exposing the bound complex to a solution having an ionic strength sufficient to separate said complex.

19. The method of claim 13 wherein said peptide consists of between approximately four and forty amino acids and comprises a sequence of at least four consecutive amino acids corresponding to amino acids 165–260 of glycoprotein Ib.

20. The method of claim 13 wherein said peptide is selected from the group consisting of PEP-12, PEP-13, PEP-14, PEP-15, PEP-16 and PEP-17.

21. A method for purifying factor VIII:C from a heterogeneous biological fluid containing factor VIII:C-von Willebrand factor complexes, comprising:

exposing the biological fluid to a peptide that specifically binds to von Willebrand factor, said peptide consisting essentially of between four and ninety-six amino acids and containing a sequence of at least four consecutive amino acids corresponding to amino acids 165–260 of glycoprotein Ib, said peptide being bound to an insoluble matrix, such that the factor VIII:C-von Willebrand factor complex specifically binds to the peptide;

eluting the bound complexes from the peptide;

dissociating the factor VIII:C-von Willebrand factor complex; and isolating the factor VIII:C.

* * * * *